United States Patent [19]
Wiegel et al.

[11] Patent Number: 5,184,275
[45] Date of Patent: Feb. 2, 1993

[54] HEEL GROUNDING DEVICE

[75] Inventors: Dave C. Wiegel, Manhattan Beach; Dan A. Bradshaw, Hawthorne; Stasys Petravicius, Ranchos Palos Verdes, all of Calif.

[73] Assignee: Hughes Aircraft Company, Los Angles, Calif.

[21] Appl. No.: 454,814

[22] Filed: Dec. 21, 1989

[51] Int. Cl.5 .................................. H05F 3/02
[52] U.S. Cl. ........................ 361/223; 36/136
[58] Field of Search .............. 361/212, 220-224; 174/5 R, 55 G, 55 B; 36/59 R, 136

[56] References Cited

U.S. PATENT DOCUMENTS

| | | | |
|---|---|---|---|
| 101,602 | 4/1870 | Fanyou | 361/224 |
| 2,712,098 | 6/1955 | Legge | 361/223 |
| 3,015,754 | 1/1962 | Legge | 361/223 |
| 3,274,442 | 9/1966 | Peel | 361/224 |
| 3,544,841 | 12/1970 | Peel | 361/224 |
| 3,846,921 | 11/1974 | Kobayashi | 36/59 R |
| 3,912,973 | 10/1975 | Young | 361/223 |
| 4,551,783 | 11/1985 | Cohen et al. | 361/223 |
| 4,639,825 | 1/1987 | Briedegam | 361/212 |

Primary Examiner—A. D. Pellinen
Assistant Examiner—David Osborn
Attorney, Agent, or Firm—L. A. Alkov; W. K. Denson-Low

[57] ABSTRACT

A heel grounding device (10) is disclosed which is used in connection with electrically grounded conductive flooring which in one embodiment is secured to the shoe (12) of a human operator. A strap (24) is secured about the leg (11) of the operator with conductive material (29) touching the operator. Grounding lead (25) attaches by a fastener (27) from conductive material (29) to partially conductive material (20) which is secured to the heel (15) of the shoe (12) of the operator. A strap (23) is used to secure the device onto the shoe (12) of the operator. Metal rivets (31, 32, 33) are secured in and protrude from partially conductive erlement so as to maintain electrical contact with the conductive grounded flooring to overcome soil build up on partially conductive material (20) and thereby maintain electrical grounding of the operator.

2 Claims, 1 Drawing Sheet

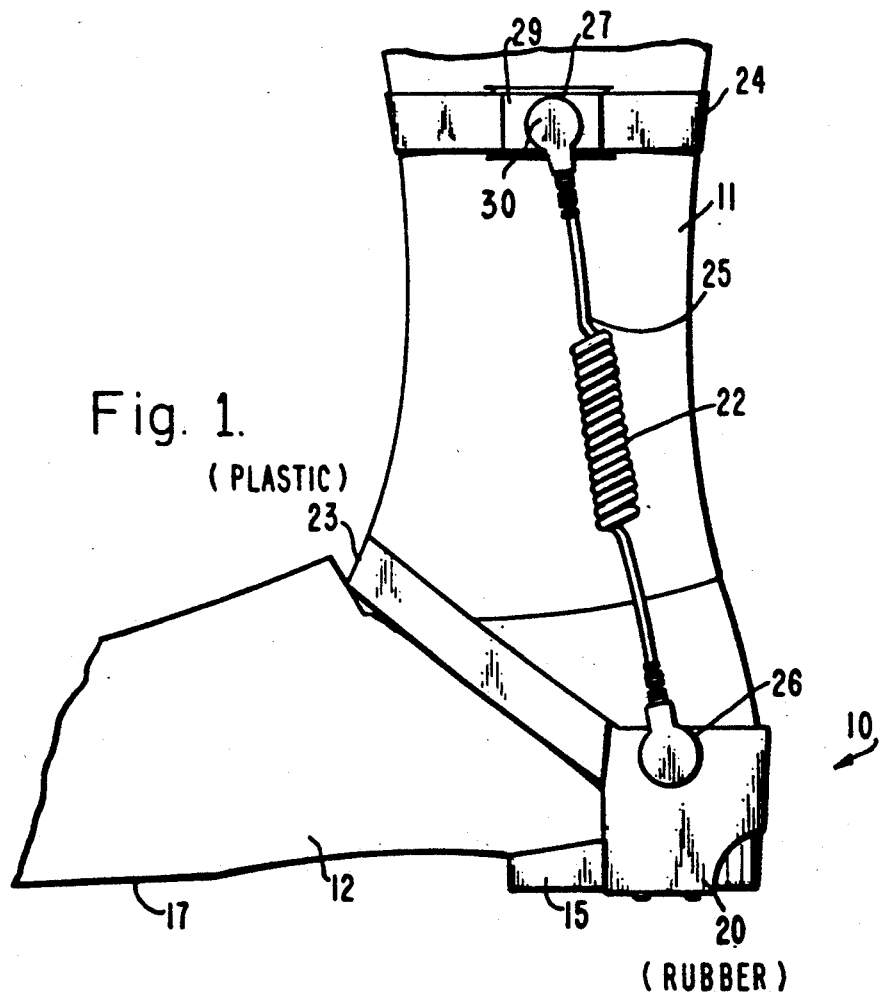
Fig. 1.
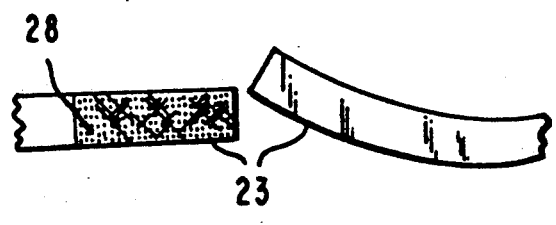
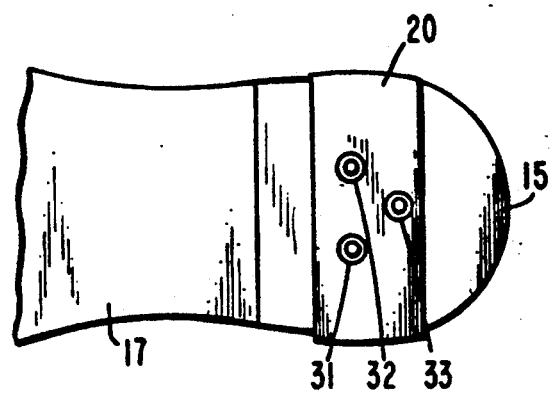
Fig. 3.
Fig. 2.

HEEL GROUNDING DEVICE

BACKGROUND OF THE INVENTION

1. Field of the Invention

This invention relates to electrostatic discharge devices, and in particular to a device worn on the heel of an operator wherein the device contains rivets which protrude from the bottom of the device to overcome soil build-up in the discharge of static electricity.

2. Description of the Related Art

In the process of contacting electronic components or parts to assemble into an electronics system, a major problem is the destruction of the parts by static electricity. A significant electrical potential difference between the part and an operator in contact with the part can cause the part to be damaged by the rapid transfer of static electricity. Due to the general existence of static electricity in the usual working environment and the expense of such electronic components, damage to these parts can easily occur and is highly undesirable.

The basic solution to the electrostatic discharge problem in the art is to provide a mechanism to an operator which electrically grounds the operator at a zero electrical potential. The electronic components to be in contact with the operator are also maintained at, or very close to, a zero electric potential. Therefore, there is generally no potential variation between the parts and the operator when they come into contact.

Examples of such electrical grounding devices are wrist strap devices worn by an operator at a work station where the operator is assembling an electronic device from parts. Because such devices have proved limiting in permitting the operator desired freedom of movement from a specific work station, a grounding device worn on the heel of the operator in contact with a special electrically grounded conductive floor was developed.

Examples of such heel grounding devices are produced by Westek of Arcadia, Calif.; the Westek Part No. M9902, a leg band that is an adjustable conductive stretch fabric with a snap with a wire (incorporating a one megohm resistor) leading from the leg band to the foot. The foot band is made of conductive rubber which makes contact with a grounded conductive floor. Westek also has shoe grounding device part Nos. MX9902M and MX9902F which tuck into the shoe and ground the operator through a 1 megohm resistor.

Also, SIMCO of Hatfield, PA produces reusable conductive heel grounders and sole grounders which provide continuous grounding of transient personnel to conductive flooring. Plastic Systems of Marlboro, MA is also a manufacturer of such devices.

A fundamental advantage of these prior art devices is that they permit the operator freedom of motion without being limited to a particular work-station.

However, a basic limitation has been encountered with prior art heel grounders. The grounders are comprised of an electrically conductive material which contacts an electrically grounded conductive floor. The devices gather soil from the conductive grounded flooring as the operator wearing the device (on his shoe) moves about. This is especially true when conductive rubber is used as worn on the heel of the operator, as the material is sticky and actually tends to attract soil from the floor as the operator moves along the floor. Even a floor that appears to be clean can have soil which builds up on the shoe of the operator. Such soil build up can actually occur within minutes. The non-electrically conducting soil acts as an insulation layer between the heel grounder and the grounded floor. As a result, electrical conductivity between the operator and the floor becomes reduced, ultimately rendering the device useless.

It would, therefore, be a great improvement in the art to have a heel grounding device which is resistant to the effects of soil accumulation.

SUMMARY OF THE INVENTION

It is therefore an object of the present invention to provide an improved heel grounder that resists the detrimental effect of soil build-up.

Another object of this invention is to provide an improved heel grounder which can be economically and easily produced for highly effective and reliable overall operation.

The present invention can be broadly stated as an electrostatic discharge device attached to an operator communicating with an electrically conductive grounding element comprising: (1) means attached to an operator for discharging static electricity from the operator, with the means being partially electrically conductive; (2) means for discharging static electrically with the means being located within the first means for discharging static electricity from the operator, the second means being electrically conductive and in communication with the conductive grounding element; (3) means connected to said operator and the first means for discharging static electricity from the operator, with the means including an electrically resistive element; and (4) means for attaching the first means for discharging static electricity from the operator to the conductive grounding element.

In a specific embodiment, the present invention can be defined as an electrostatic discharge device attached to a human operator standing or walking on a conductive grounded floor comprising: (1) a partially electrically conductive element worn against the heel of the shoe of the operator; (2) conductive elements located within and protruding from the partially electrically conductive element and communicating with the conductive grounded flooring; (3) an electrically conductive strap with a ground lead containing an electrical resistor, one end of which is attached to the partially electrically conductive element worn by the operator and the other end is attached to the skin of the operator; and (4) a connecting strap with one end connected to the partially conductive element.

BRIEF DESCRIPTION OF THE DRAWINGS

The features of a specific embodiment of the best mode contemplated of carrying out the invention are illustrated in the drawing, in which:

FIG. 1 is a pictorial view of the device as it is worn by and to be used by an operator; and FIG. 2 is a bottom view of the device.

FIG. 3 describes the configuration of the strap which accommodates wearing the device by the operator.

DESCRIPTION OF THE PREFERRED EMBODIMENTS

FIG. 1 depicts an embodiment of the electrostatic discharge invention as worn by a human operator as heel grounder 10. The operator is assumed to be standing or walking on conductive grounded flooring.

A partially conductive element 20 is placed against the heel 15 of shoe 12 as worn by the operator. Typically, element 20 is made of a carbonized rubber material. Such material is produced by Plastic Systems of Marlboro, Mass. However, it is possible to use other materials that conduct electricity, and which can be easily secured to the heel of the shoe 12 of the operator.

Strap 23 is attached to conductive element 20, with a strong adhesive. Such adhesive is readily available in the market place. Strap 23 can also be sewn or otherwise attached to conductive element 20. Strap 23 is intended to accommodate wearing heel grounder 10 by the operator. Strap 23 is placed snugly over the top of shoe 12 of the operator to maintain heel ground 10 in proper position. Strap 23 generally consists of two pieces, each separately attached to opposite sides of the conductive element 20; one of such pieces is shown in FIG. 1 as so attached. Strap 23 can be made of a plastic material consisting of two pieces with a velcro material 28 hook and pile attachment configuration, to easily attach to shoe 12, the hook being on the bottom of one piece and the pile on the top of the other, or vice versa. This configuration for strap 23 is shown in FIG. 3. Both the plastic material and the velcro material are commercially available. In another embodiment, two separate straps can be attached one to each side of conductive element 20 to be tied together by the operator. Other methods to secure the straps together are also available such as snap fasteners on each end of the separate pieces of strap 23. Strap 23 can also consist of a plurality of pieces comprising the strap.

Strap 24 is worn about the leg of the operator. Strap 24 is made of elastic fabric to easily conform to the leg of the operator, with an electrically conductive material 29 inserted within strap 24 which touches the skin of the leg of the operator. Material 29 is usually a buckle attached to strap 24. Material 29 may be a carbonized rubber material or a metal. One end of snap fastener 27 is attached to or embedded in material 29. The other end of snap fastener 27 is attached to ground lead 25 which has one end of snap fastener 26 on the other end. The other end of snap fastener 26 is attached to partially conductive element 20. Ground lead 25 has coil 22 which can elongate or contract to accommodate the movement of the operator. Snap fasteners 26 and 27 are made of conductive material and are readily commercially available. Also contained in ground lead 25 is an electrically resistive element 30, such as a resistor. Typically, the resistor has a value of one megohm.

Heel grounder 10 functions to dissipate electrostatic electricity from the operator in the following manner; Static electricity of the operator is conducted through conductive material 29 through snap fastener 27 through ground lead 25 to snap fastener 26 to partially conductive element 20. When the operator is walking on conductive grounded flooring, in appropriate operation, static electricity dissipates from conductive element 20 to the floor. Consequently, when properly worn by an operator as he stands or walks on a grounded conductive flooring, the operator is grounded to effectively zero electrical potential.

FIG. 2 depicts a view of the bottom of shoe 12 with sole 17 and heel 15. Partially conductive element 20 is shown as attached to heel 15.

Electrically conductive elements 31, 32, 33 are shown embedded in and protrude from conductive element 20. Elements 31, 32 and 33 extend slightly on the order of 1/32" to 1/16" from conductive element 20, so as to not discomfort the operator as he walks on electrically conductive grounded flooring.

Electrically conductive elements are generally made of metal. An example of elements 31, 32 and 33 are metal rivets which can be readily embodied in conductive element 20. Metal rivets are commercially available and can be easily adapted for the use in the heel grounding device 10. McMaster-Carr is a typical supplier of such rivets. However, elements 31, 32, 33 can be made of other materials.

Elements 31, 32 and 33 are embedded in conductive material 20 by a typical rivet press or by cutting away a small amount of material from conductive material 20, to separately accommodate each of elements 31, 32 and 33.

FIG. 2 shows elements 31, 32 and 33 embedded in conductive material 20 in a triangular configuration. This configuration has been found to be comfortable when worn by an operator as he walks with the heel grounder. However, other configurations can be used, such as a single element or rivet, or a narrow or wide strip of conductive material.

With elements 31, 32 and 33 protruding from conductive element 20, soil which customarily builds up on conductive element 20 to inhibit electrical conductivity will have no effect on such conductivity.

In fact, it has been found that as an operator moves about on the floor, the action of the rivets against the floor tends to polish the rivets for a self-cleaning effect.

In operation, using personnel place conductive element 20 on the heel of one shoe. Strap 23 is used by using personnel to secure the grounding device to shoe 12. When velcro is used, the operator merely engages the two pieces of strap 23 together in standard velcro hook and pile configuration on the top of shoe 12. Strap 24 is secured around the leg of the operator so as to touch his skin. Snap fastener 27 of electrically conductive lead 25 is attached to strap 24 by the operator. The other end of lead 25 is attached by the operator to partially conductive element 20 by snap fastener 26. In this configuration, with heel grounder 10 secured to the operator, as the operator stands or walks on conductive grounded flooring in the work area where he is touching electronic components, static electricity is dissipated from the operator to the floor. With electronic components which the operator touches also being maintained at zero electrical potential, by some electrostatic discharge device, there is no static discharge to the component. In this way, electronic components are not damaged by static electricity.

Furthermore, soil build-up due to the operator walking on the floor, though not prevented, does not prohibit the dissipation of static electricity, because the elements protrude through the bottom of conductive element 20, so as to maintain electrical contact with the floor.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention.

I claim:

1. An electrostatic discharge device attached to an operator communicating with an electrically conductive grounding element comprising:

partially electronically conductive element (20) composed of carbonized rubber material attached to the operator worn against the heel (15) of a shoe (20) of the operator;

a plurality of metal rivets (31, 32, 33) arranged in a triangular configuration protruding no more than 1/16 inch from said partially electronically conductive element (20) for discharging static electricity for the safety and comfort of the operator;

a ground lead (25) with a first fastener (27) containing an electrical resistor (30) therein and a second fastener (26), said ground lead having a coil (22) which can elongate or contact, and is connected to said partially conductive element (20) by said second fastener (26);

a first strap (23) connected to said partially conductive element (20), said first strap consisting of plastic material consisting of two pieces with a velcro material in a hook and pile attachment configuration; and a second strap (24) made of elastic fabric attached using a metal buckle (29) to a leg of said operator by said first fastener (27) of said lead (25) and said partially conductive element (20) by way of said lead (25) with said second fastener (26).

2. The electronic discharge device of claim 1 wherein said plurality of metal rivets protruding from said partially conductive element consist of three said rivets arranged in a triangular configuration.

* * * * *